US010688109B1

(12) United States Patent
Oates et al.

(10) Patent No.: US 10,688,109 B1
(45) Date of Patent: Jun. 23, 2020

(54) METHODS OF PREVENTING PLATELET ACTIVATION

(71) Applicant: Vanderbilt University, Nashville, TN (US)

(72) Inventors: John A. Oates, Nashville, TN (US); Olivier Boutaud, Nashville, TN (US); Irene Zagol-Ikapitte, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/200,403

(22) Filed: Nov. 26, 2018

Related U.S. Application Data

(62) Division of application No. 15/387,507, filed on Dec. 21, 2016, now Pat. No. 10,166,248.

(60) Provisional application No. 62/270,435, filed on Dec. 21, 2015.

(51) Int. Cl.
| *A61K 31/609* | (2006.01) |
| *A01N 1/02* | (2006.01) |
| *A61P 7/06* | (2006.01) |
| *A61P 7/02* | (2006.01) |
| *A61P 7/00* | (2006.01) |

(52) U.S. Cl.
CPC .......... *A61K 31/609* (2013.01); *A01N 1/0226* (2013.01); *A61P 7/00* (2018.01); *A61P 7/02* (2018.01); *A61P 7/06* (2018.01)

(58) Field of Classification Search
CPC . A61K 31/609; A61P 7/00; A61P 7/02; A61P 7/06; A01N 1/0226
See application file for complete search history.

(56) References Cited

U.S. PATENT DOCUMENTS

| 7,705,054 | B1 | 4/2010 | Roberts, II | |
| 8,063,101 | B2* | 11/2011 | Lockwood | A61K 31/01 514/460 |
| 10,166,248 | B1* | 1/2019 | Oates | A61P 7/00 |
| 2007/0082840 | A1* | 4/2007 | Porter | A61K 31/445 514/183 |
| 2009/0186810 | A1* | 7/2009 | Zwaal | A61K 31/4745 514/1.1 |
| 2014/0256774 | A1 | 9/2014 | Roberts, II | |
| 2015/0265584 | A1* | 9/2015 | Oates | A61K 31/44 514/351 |

OTHER PUBLICATIONS

Mehta et al., "Spontaneous Platelet Aggregation: Observations on Potential Mechanisms", 1987, Thrombosis Research, 45(3), pp. 249-256. (Year: 1987).*

Parker et al., "Effect of aspirin on platelet-von Willebrand factor surface expression on thrombin and ADP-stimulated platelets", 1989, Blood, 74(6), pp. 2016-2021. (Year: 1989).*
Hecker, M., M. Haurand, V. Ullrich, U. Diczfalusy, and S. Hammarstrom. Products, kinetics, and substrate specificity of homogeneous thromboxane synthase from human platelets: development of a novel enzyme assay. Arch Biochem Biophys; 1987; 254: 124-135.
Shao, B., S. Pennathur, I. Pagani, M. N. Oda, J. L. Witztum, J. F. Oram, and J. W. Heinecke. 2010. Modifying apolipoprotein A-I by malondialdehyde, but not by an array of other reactive carbonyls, blocks cholesterol efflux by the ABCA1 pathway. J. Biol. Chem. 285: 18473-18484.
Uchida, K. Role of reactive aldehyde in cardiovascular diseases. Free Radic Biol Med 2000. 28: pp. 1685-1696.
Zagol-Ikapitte, I., V. Amarnath, M. Bala, L. J. Roberts, 2nd, J. A. Oates, and O. Boutaud. 2010. Characterization of scavengers of gamma-ketoaldehydes that do not inhibit prostaglandin biosynthesis. Chem. Res. Toxicol. 23: 240-250.
US Department of Health and Human Services, F. a. D. A., Center for Drug Evaluation and Research, Center for Veterinary Medicine. 2001. US DHHS, FAD, CDER. Guidance for Industry: Bioanalytical Method Validation. In Available at: http://www.fda.gov/cder/guidance/4252fnl.pdf.
Grundy, S. M., J. I. Cleeman, S. R. Daniels, K. A. Donato, R. H. Eckel, B. A. Franklin, D. J. Gordon, R. M. Krauss, P. J. Savage, S. C. Smith, Jr., J. A. Spertus, F. Costa, A. American Heart, L. National Heart, and I. Blood. 2005. Diagnosis and management of the metabolic syndrome: an American Heart Association/National Heart, Lung, and Blood Institute Scientific Statement. Circulation 112: 2735-2752.
Boutaud, O., J. Li, I. Zagol, E. A. Shipp, S. S. Davies, L. J. Roberts, 2nd, and J. A. Oates. 2003. Levuglandinyl adducts of proteins are formed via a prostaglandin H2 synthase-dependent pathway after platelet activation. J. Biol. Chem. 278: 16926-16928.
Sugimori, H., F Tomoda, T. Koike, H. Kinuno, H. Kurosaki, T. Masutani, and H. Inoue. 2012. Blood rheology and platelet function in untreated early-stage essential hypertensives complicated with metabolic syndrome. Int J Hypertens 2012: 109830.
Santilli, F., N. Vazzana, R. Liani, M. T. Guagnano, and G. Davi. 2012. Platelet activation in obesity and metabolic syndrome. Obes Rev 13: 27-42.
Smith, J. P., E. V. Haddad, M. B. Taylor, D. Oram, D. Blakemore, Q. Chen, O. Boutaud, and J. A. Oates. 2012. Suboptimal inhibition of platelet cyclooxygenase-1 by aspirin in metabolic syndrome. Hypertension 59: 719-725.
Koike, Y., A. Yoneyama, J. Shirai, T. Ishida, E. Shoda, K. Miyazaki, S. Sunaga, R. Horie, K. Aoki, K. Koike, I. Ogata, T. Tahara, T. Kato, K. Nakahara, T. Kariya, and M. Higashihara. 1998. Evaluation of thrombopoiesis in thrombocytopenic disorders by simultaneous measurement of reticulated platelets of whole blood and serum thrombopoietin concentrations. Thromb. Haemost. 79: 1106-1110.
Faull, R. J., X. Du, and M. H. Ginsberg. 1994. Receptors on platelets. Methods Enzymol. 245: 183-194.
2005. Heart disease and stroke statistics. Am Heart Assoc Update. Dallas, Texas.

(Continued)

*Primary Examiner* — My-Chau T. Tran
(74) *Attorney, Agent, or Firm* — Stites & Harbison PLLC; Richard S. Myers, Jr.

(57) ABSTRACT

A method of preventing or reducing the occurrence of malondiadehyde and/or levuglandin protein modification in a subject in need thereof, comprising administering to said subject an effective amount of at least one γ-KA scavenger compound, or a pharmaceutically acceptable salt thereof.

7 Claims, 5 Drawing Sheets

(56) References Cited

OTHER PUBLICATIONS

Serebruany, V. L., A. Malinin, S. Ong, and D. Atar. 2008. Patients with metabolic syndrome exhibit higher platelet activity than those with conventional risk factors for vascular disease. J Thromb Thrombolysis 25: 207-213.

Vaduganathan, M., C. L. Alviar, M. E. Arikan, A. Tellez, S. Guthikonda, T. DeLao, J. F. Granada, N. S. Kleiman, C. M. Ballantyne, and E. I. Lev. 2008. Platelet reactivity and response to aspirin in subjects with the metabolic syndrome. Am Heart J 156: 1002 e1001-1002 e1007.

Vaidya, D., L. R. Yanek, N. Faraday, T. F. Moy, L. C. Becker, and D. M. Becker. 2009. Native platelet aggregation and response to aspirin in persons with the metabolic syndrome and its components. Metab Syndr Relat Disord 7: 289-296.

Arteaga, R. B., J. A. Chirinos, A. O. Soriano, W. Jy, L. Horstman, J. J. Jimenez, A. Mendez, A. Ferreira, E. de Marchena, and Y. S. Ahn. 2006. Endothelial microparticles and platelet and leukocyte activation in patients with the metabolic syndrome. Am. J. Cardiol. 98: 70-74.

Gokulakrishnan, K., R. Deepa, V. Mohan, and M. D. Gross. 2006. Soluble P-selectin and CD40L levels in subjects with prediabetes, diabetes mellitus, and metabolic syndrome—the Chennai Urban Rural Epidemiology Study. Metabolism 55: 237-242.

Natal, C., P. Restituto, C. Inigo, I. Colina, J. Diez, and N. Varo. 2008. The proinflammatory mediator CD40 ligand is increased in the metabolic syndrome and modulated by adiponectin. J Clin Endocrinol Metab 93: 2319-2327.

Pignatelli, P., V. Sanguigni, L. Lenti, D. Ferro, A. Finocchi, P. Rossi, and F. Violi. 2004. gp91phox-dependent expression of platelet CD40 ligand. Circulation 110: 1326-1329.

Ford, E. S., A. H. Mokdad, W. H. Giles, and D. W. Brown. 2003. The metabolic syndrome and antioxidant concentrations: findings from the Third National Health and Nutrition Examination Survey. Diabetes 52: 2346-2352.

Palmieri, V. O., I. Grattagliano, P. Portincasa, and G. Palasciano 2006. Systemic oxidative alterations are associated with visceral adiposity and liver steatosis in patients with metabolic syndrome. J Nutr 136: 3022-3026.

Roberts, L. J., 2nd, B. J. Sweetman, N. A. Payne, and J. A. Oates. 1977. Metabolism of thromboxane B2 in man. Identification of the major urinary metabolite. J. Biol. Chem. 252: 7415-7417.

Catella, F., and G. A. FitzGerald. 1987. Paired analysis of urinary thromboxane B2 metabolites in humans. Thromb Res 47: 647-656.

McAdam, B. F., D. Byrne, J. D. Morrow, and J. A. Oates. 2005. Contribution of cyclooxygenase-2 to elevated biosynthesis of thromboxane A2 and prostacyclin in cigarette smokers. Circulation 112: 1024-1029.

Fitzgerald, D. J., L. Roy, F. Catella, and G. A. FitzGerald. 1986. Platelet activation in unstable coronary disease. N. Engl. J. Med. 315: 983-989.

Lellouche, F., M. Martinuzzo, P. Said, J. Maclouf, and L. O. Carreras. 1991. Imbalance of thromboxane/prostacyclin biosynthesis in patients with lupus anticoagulant. Blood 78: 2894-2899.

Martinuzzo, M. E., R. R. Forastiero, L. Kordich, and L. O. Carreras. 2001. Increased lipid peroxidation correlates with platelet activation but not with markers of endothelial cell and blood coagulation activation in patients with antiphospholipid antibodies. Br J Haematol 114: 845-851.

Blache, D., T. Gautier, U. J. Tietge, and L. Lagrost. 2012. Activated platelets contribute to oxidized low-density lipoproteins and dysfunctional high-density lipoproteins through a phospholipase A2-dependent mechanism. FASEB J 26: 927-937.

Choi, J. W., J. H. Kim, S. C. Cho, M. K. Ha, K. Y. Song, H. D. Youn, and S. C. Park. 2011. Malondialdehyde inhibits an AMPK-mediated nuclear translocation and repression activity of ALDH2 in transcription. Biochem Biophys Res Commun 404: 400-406.

Besler, C., K. Heinrich, L. Rohrer, C. Doerries, M. Riwanto, D. M. Shih, A. Chroni, K. Yonekawa, S. Stein, N. Schaefer, M. Mueller, A. Akhmedov, G. Daniil, C. Manes, C. Templin, C. Wyss, W. Maier, F. C. Tanner, C. M. Matter, R. Corti, C. Furlong, A. J. Lusis, A. von Eckardstein, A. M. Fogelman, T. F. Luscher, and U. Landmesser. 2011. Mechanisms underlying adverse effects of HDL on eNOS-activating pathways in patients with coronary artery disease. J. Clin. Invest. 121: 2693-2708.

\* cited by examiner ary of U.S. application Ser.
METHODS OF PREVENTING PLATELET ACTIVATION

PRIOR APPLICATIONS

This application is a divisional of U.S. application Ser. No. 15/387,507, now allowed, which claims benefit to U.S. Application No. 62/270,435, filed Dec. 21, 2015; the contents of both applications are incorporated herein by reference in their entirety.

GOVERNMENT INTEREST

This invention was made with government support under grant numbers GM087603 and P50HL81009 awarded by the National Institutes of Health. The government has certain rights in the invention.

INTRODUCTION AND SUMMARY

Analysis of platelet activation is typically done on fresh blood because platelets are very quickly activated after blood is drawn. Current inhibitors of platelet activation used at time of phlebotomy do not sufficiently prevent platelet activation if the tubes of blood are not quickly used for analysis. It is therefore recommended in the field that platelet analysis be done within 2 hours post drawing. This time constraint restricts the ability to do large scale testing and to centralize platelet analysis in a multicenter study. The present invention allows analysis, e.g., by flow cytometry, of platelet activation of blood drawn up to about 72 hours before analysis.

The present invention is also directed to methods of prevention of malondialdehyde modification of platelet proteins. The thromboxane synthase converts prostaglandin $H_2$ to thromboxane $A_2$ and malondialdehyde (MDA) in approximately equimolar amounts. A reactive dicarbonyl, MDA forms covalent adducts of amino groups, including the ε-amine of lysine. Utilizing a novel LC/MS/MS method for analysis of one of the MDA adducts, the dilysyl-MDA crosslink, the present inventors have demonstrated that dilysyl-MDA crosslinks in human platelets are formed following platelet activation via the COX-1/thromboxane synthase pathway. Compounds of the present invention were shown to react with MDA preferentially, thereby preventing formation of lysine adducts. Dilysyl-MDA crosslinks were measured in two diseases known to be associated with increased platelet activation. Levels of platelet dilysyl-MDA crosslinks were increased by 2 fold in metabolic syndrome relative to healthy subjects, and by 1.9 fold in sickle cell disease. In patients with sickle cell disease, the reduction of platelet dilysyl-MDA crosslinks following NSAID administration provided evidence that MDA modifications of platelet proteins in this disease are derived from the cyclooxygenase pathway. In summary, MDA adducts of platelet proteins that crosslink lysines are formed on platelet activation and are increased in diseases associated with platelet activation. These protein modifications can be prevented by salicylamine-related scavengers.

Thus, another aspect of the present invention is a method of preventing the formation of malondialdehyde adducts. Another aspect of the present invention is a method of protecting histones and DNA from reactive dicarbonyls.

Another aspect of the present invention is the inhibition of platelet activation.

Another aspect of the present invention is a method of preventing or reducing the occurrence of malondiadehyde and/or levuglandin protein modification in a subject in need thereof, comprising administering to said subject an effective amount of at least one γ-KA scavenger compound, or a pharmaceutically acceptable salt thereof.

Another aspect of the present invention is a method of preventing the formation of malondiadehyde adducts, comprising administering to a subject in need thereof an effective malondiadehyde adduct reducing amount of a of at least one γ-KA scavenger compound, or a pharmaceutically acceptable salt thereof.

Another aspect of the present invention is a method of inhibiting platelet activation, comprising administering to a subject in need thereof an effective malondiadehyde adduct reducing amount of a of at least one γ-KA scavenger compound, or a pharmaceutically acceptable salt thereof.

Another aspect of the present invention is a method of treating sickle cell anemia.

Another aspect of the present invention is a method of treating metabolic syndrome.

Another aspect of the present invention is method of treating thrombosis.

for 40 min, followed by arachidonic acid (at 5 μM final concentration) for an additional 2 h. Scavengers-MDA adducts were extracted with ethyl acetate, and analyzed by LC/MS/MS by monitoring the specific SRM transitions of m/z 208→136 (SA-MDA) and 178→106 (MoSA-MDA). +p<0.0001 vs subject or AA. One-way ANOVA followed by Tukey's multiple comparisons test was used. (n >7).

Figure 6:
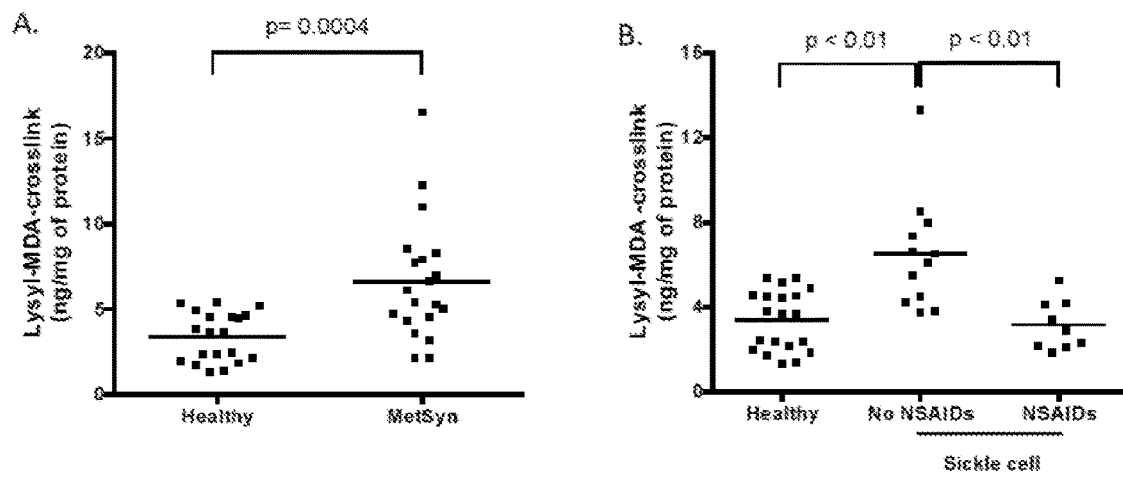

FIG. 6 are graphs that show dilysyl-MDA crosslinks isolated from washed platelets of patients with MetSyn or SCD. The dilysyl-MDA crosslink was purified and analyzed by LC/MS/MS. (A) Levels of dilysyl-MDA crosslinks were 2-fold higher in un-activated platelets from MetSyn patients (n=25) than healthy volunteers (n=20, p=0.0002 by t-test (two-tailed) with welch's correction). (B) In platelets from SCD patients with no NSAIDs (n=12), levels of dilysyl-MDA crosslinks were 2-fold higher than from healthy volunteers (n=20, p<0.0001, SCD no NSAIDs vs healthy patients or vs SCD NSAIDs patients). One-way ANOVA followed by Tukey's multiple comparisons test was used. The bars represent the mean for each category. No statistical significance was found between Healthy volunteers and SCD NSAIDs (n=9) patients.

Figure 7:
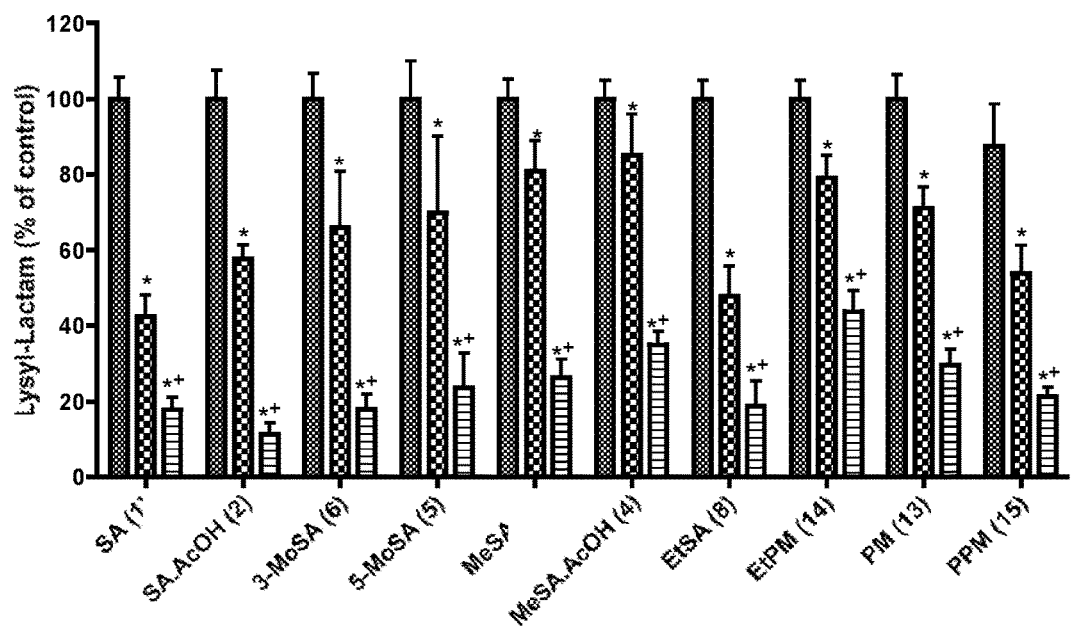

FIG. 7 is a graph that shows inhibition of formation of LG adducts in platelets for an embodiment of the present invention.

Figure 8:
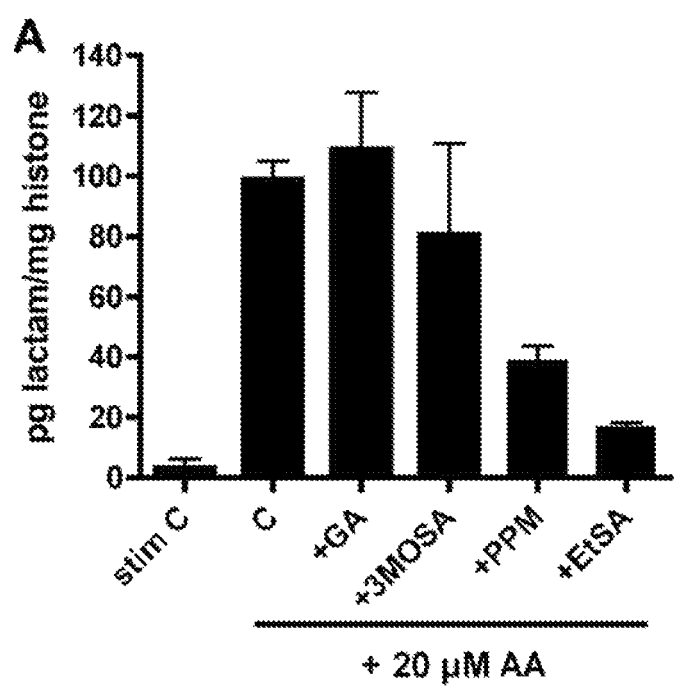

FIG. 8 is graph that shows the scavenger EtSA blocks LG-lysyl adduct formation on histones.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As can be seen herein, there is overlap in the definition of treating and preventing.

As used herein, the term "diagnosed" means having been subjected to a physical examination by a person of skill, for example, a physician, and found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. For example, a subject can be identified as having a need for treatment of a disorder (e.g., a disorder related to inflammation) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "scavenger" or "scavenging" refers to a chemical substance that can be administered in order to remove or inactivate impurities or unwanted reaction products. For example, the isoketals irreversibly adduct specifically to lysine residues on proteins. The isoketal scavengers of the present invention react with isoketals before they adduct to the lysine residues. Accordingly, the compounds of the present invention "scavenge" isoketals, thereby preventing them from adducting to proteins.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The terms "amine" or "amino" as used herein are represented by a formula $NA^1A^2A_3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "hydroxyl" as used herein is represented by a formula —OH.

The term "nitro" as used herein is represented by a formula —$NO_2$.

The term "pharmaceutically acceptable" describes a material that is not biologically or otherwise undesirable, i.e., without causing an unacceptable level of undesirable biological effects or interacting in a deleterious manner.

Examples of compounds of the present invention include, but are not limited to, compounds selected from the formula:

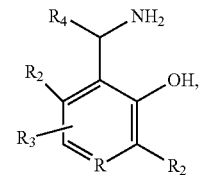

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; and
pharmaceutically acceptable salts thereof.

The compound may be chosen from:

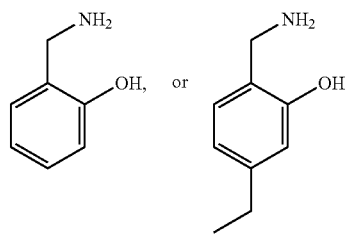

or a pharmaceutically acceptable salt thereof.

The compound may also be chosen from:

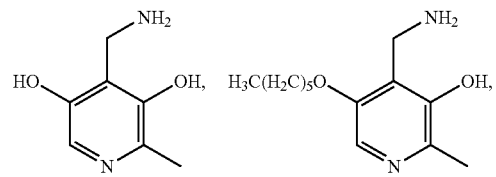

-continued

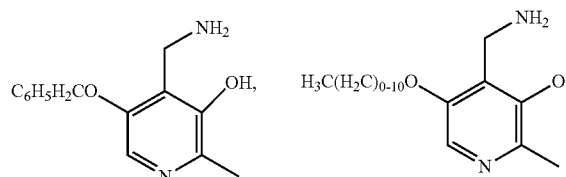

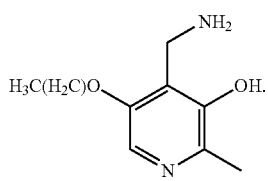

or a pharmaceutically acceptable salt thereof.

The compounds or analogs may also be chosen from:

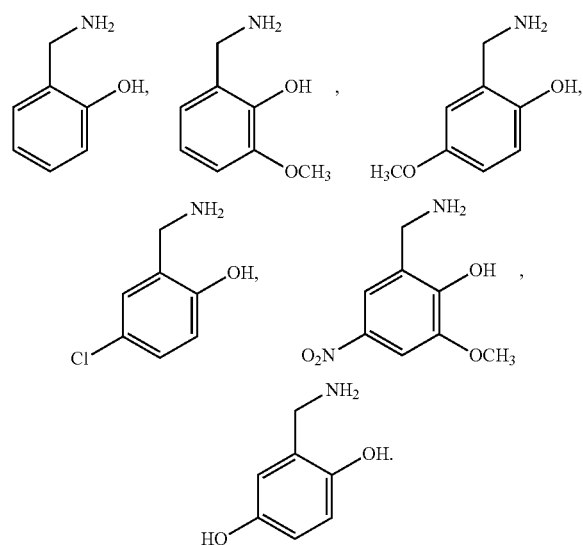

or a pharmaceutically acceptable salt thereof.

The compounds may also be chosen from:

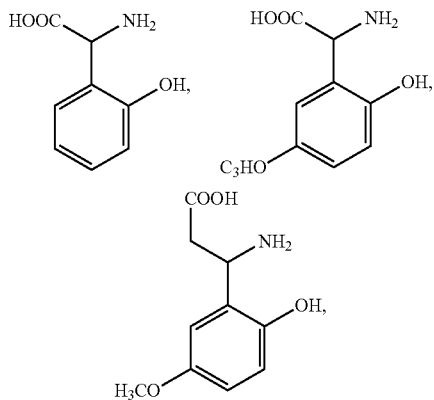

or a pharmaceutically acceptable salt thereof.

The compounds may also be chosen from

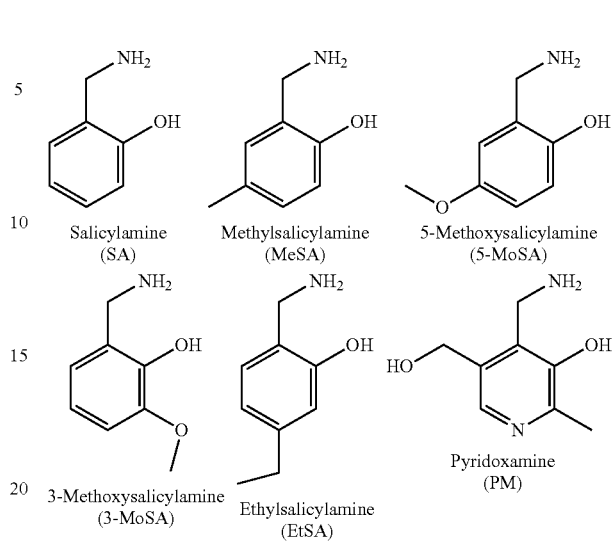

Salicylamine (SA)   Methylsalicylamine (MeSA)   5-Methoxysalicylamine (5-MoSA)

3-Methoxysalicylamine (3-MoSA)   Ethylsalicylamine (EtSA)   Pyridoxamine (PM)

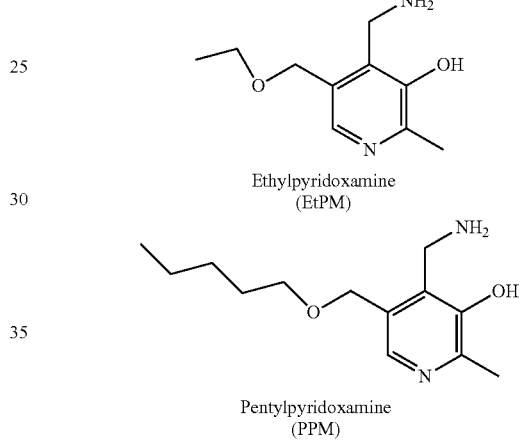

Ethylpyridoxamine (EtPM)

Pentylpyridoxamine (PPM)

or a pharmaceutically acceptable salt thereof.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Embodiments of the present invention also include a composition comprising a mixture of components, which the present inventors discovered to be useful for platelet stabilization or prevention of platelet activation of drawn blood. The beneficial features of this composition allow platelet analysis of the drawn blood to be conducted more than 2 hours post-draw and in some embodiments, up to about 72 hours post-draw. The composition, kits, and methods of the presently-disclosed subject matter can be used to "fix" the platelets in the activation state in which they were at the time of blood drawing.

In some embodiments, the composition includes an irreversible inhibitor of COX-1 together with a series of compounds for limiting or substantially preventing activation of the reinforcement pathway of platelets, including a compound for blocking activation of the purinergic receptors, a compound for blocking the thromboxane receptor, a compound for increasing intracellular cAMP concentration, and a compound that blocks potassium-dependent coagulation factors. In some embodiments, the composition further includes a compound that is a reactive aldehyde scavenger that protects platelet proteins from covalent modification by dicarbonyls, which are also products of COX-1 activity and oxidative stress.

In some embodiments, the composition includes EDTA (blocks potassium-dependent coagulation factors), aspirin (COX-1 inhibitor), apyrase (blocks activation of the purinergic receptors), carbaprostacyclin (increases intracellular cAMP concentration), and SQ 29,548 (blocks the thromboxane receptor). In some embodiments, the composition further includes pyridoxamine (aldehyde scavenger). In some embodiments, for each about 5 ml of blood, the composition includes EDTA (about 9 mg), aspirin (100 μM), apyrase (2 Units), carbaprostacyclin (1 μM), SQ 29,548 (10 nM) and pyridoxamine (1 mM) final concentration.

The presently-disclosed subject matter further includes kits. The kits can include a phlebotomy tube, vacutainer tube, syringe, or other device for collecting blood, packaged together with the composition of the presently disclosed subject matter. In some embodiments, the composition is contained within the device for collecting blood.

The presently-disclosed subject matter further includes methods. In some embodiments, the method involves contacting collected blood with an amount of the composition that is effective for substantially preventing or reducing platelet activation. In some embodiments, the method involves collecting blood using a device that contains the composition.

In some embodiments of the presently-disclosed subject matter, blood is collected into a 5 ml syringe containing 9 mg EDTA, aspirin (100 μM), apyrase (2 Units), carbaprostacyclin (1 μM), SQ 29,548 (10 nM) and pyridoxamine (1 mM) final concentration, to prevent ex vivo platelet activation. The blood is incubated at room temperature for 40 min. Following this incubation, blood can be stored at 4° C. or shipped in coldpack to the place where the analyses are done.

For purposes of the presently-disclosed subject matter, prevention of platelet activation can be assessed by measuring expression of P-selectin at a time-point of interest, e.g., 72 hours, post-draw. Efficacy can be tested using markers of platelet activation, including malondialdehyde adducts on proteins by mass spectrometry and platelet expression of P-selectin by flow cytometry. Other markers of platelet activation include, activated GPIIb3a, platelet-monocyte aggregates and platelet-monocyte aggregate-associated P-selectin expression.

The present inventors have demonstrated that platelet activation leads to formation of MDA adducts of platelet proteins via the COX-1/thromboxane synthase pathway. Metabolism of $PGH_2$ by the thromboxane synthase yields MDA in amounts approximately equivalent to thromboxane $A_2$ (1). As a reactive 1,3-dicarbonyl, MDA forms adducts of proteins, such as the M-propenal-lysine, that can further react with an additional amino group to form intra- and inter-molecular crosslinks.

Evidence that MDA adducts of platelet proteins are formed during activation of platelets ex vivo engendered the hypothesis that these modifications of platelet proteins also would occur in diseases in which platelet activation occurs in vivo. Development of an LC/MS/MS method for analysis of one of these adducts (the dilysyl-MDA crosslink) has made it possible to address this hypothesis.

Platelet function is disordered in MetSyn. Platelets from these patients are hyperactive when studied ex vivo (14-16), and there is evidence for in vivo platelet activation (14, 15, 17-19). The present inventors have found that dilysyl-MDA crosslinks are elevated in MetSyn to a mean level 2-fold greater than normal (p=0.0002), and 52% of the patients had values greater than the upper limit of the normal range. Platelet activation also is a feature of SCD, and levels of dilysyl-MDA crosslinks also are increased in platelets from patients with this disease (p<0.0001). Thus, increased levels of MDA adducts of platelet proteins are correlated with diseases that produce platelet activation, recapitulating the formation of these adducts during ex vivo platelet activation. These findings show that analysis of dilysyl-MDA crosslinks could provide biomarker and therapeutic options for in vivo platelet dysfunction.

The origin of the MDA adducts from the platelet COX-1/thromboxane synthase pathway is clearly demonstrated in the experiments with normal platelets activated ex vivo, in which aspirin and the thromboxane synthase inhibitor, ozagrel, reduce the dilysyl-MDA crosslinks to the levels in non-activated platelets. A major contribution of the COX-1 pathway to the increased formation of dilysyl-MDA crosslinks SCD also is suggested by the finding that therapeutic use of the cyclooxygenase inhibitor, ketorolac, in these patients was associated with a reduction of dilysyl-MDA crosslinks to the level found in normal platelets; this occurred in conjunction with a 69% reduction in serum $TxB_2$. However, MDA also is a product of radical catalyzed lipid peroxidation and reactive oxygen species are generated by platelet activation (20). Whereas normal platelets have robust anti-oxidant defenses and virtually all of MDA adduct formation is COX-1 derived, oxidant stress is evident in platelets in MetSyn. The present inventors have found an increase in $F_2$-isoprostanes esterified to platelet lipids in MetSyn, and ascorbate levels are decreased (21, 22). Thus, it is possible that in diseases such as MetSyn, platelet activation could generate MDA via radical catalyzed lipid peroxidation in addition to that generated via COX-1. If that were the case in MetSyn, the in vivo formation of MDA-protein adducts as a marker of platelet dysfunction would be amplified.

These findings provide a basis for considering the dilysyl-MDA crosslink as a biomarker of in vivo platelet dysfunction in MetSyn. The alternative approach to assessing platelet activation-induced metabolism of arachidonic acid via the COX-1/thromboxane synthase pathway is based on our discovery that 11-dehydrothromboxane $B_2$ (TxM) is a major metabolite of $TxB_2$ in humans (23). An average of 70-80% of urinary TxM is derived from platelets (24), but the amount from non-platelet sources is highly variable (10, 24, 25). Thus, the urinary excretion of TxM has been a useful indicator of large increases in platelet activation such as occurs in the acute coronary syndrome (26) and the anti-phospholipid antibody syndrome (27, 28). However, to assess individual changes in urinary TxM closer to the normal range is problematic because the amounts derived from non-platelet sources is variable; for example, non-platelet production of $TxB_2$ is increased in smokers (25). By contrast, formation of MDA specifically in the platelet is the likely source of virtually all of the dilysyl-MDA crosslinks in platelets.

Compound of the present invention, including SA and its analogues 3-MoSA, EtSA and MeSA prevent formation of MDA adducts of platelet proteins. Demonstration that MDA reacts preferentially with these scavengers to form covalent adducts of the scavengers provides a mechanism for their ability to protect proteins from the attack of MDA. In addition to the COX-1 dependent formation of the 1,3-dicarbonyl, MDA, upon platelet activation, platelet COX-1 also is the source of highly reactive 1,4-dicarbonyls, the levuglandins, which are formed from rearrangement of $PGH_2$. The present inventors previously have shown that SA also reacts with the levuglandins to prevent formation of levuglandinyl adducts of platelet proteins (4). Thus, these 2-hydroxybenzylamines are highly reactive with both 1,3- and 1,4-dicarbonyls, acting to scavenge these and similar dicarbonyls to prevent them from reacting with amino groups of cellular molecules. The efficacy of these scavengers to prevent protein modification by MDA and levuglandins in the platelet can be extended to other cells and to lipoproteins.

Accordingly, one embodiment of the present invention is a method of preventing or reducing the occurrence of malondiadehyde and/or levuglandin protein modification in a subject in need thereof, comprising administering to said subject an effective amount of at least one γ-KA scavenger compound, or a pharmaceutically acceptable salt thereof.

Another embodiment of the present invention is a method of preventing the formation of malondiadehyde adducts, comprising administering to a subject in need thereof an effective malondiadehyde adduct reducing amount of a of at least one γ-KA scavenger compound, or a pharmaceutically acceptable salt thereof.

Another embodiment of the present invention is a method of inhibiting platelet activation, comprising administering to a subject in need thereof an effective malondiadehyde adduct reducing amount of a of at least one γ-KA scavenger compound, or a pharmaceutically acceptable salt thereof.

In aspects of the invention, the subject has or is at greater risk than the general population for a disease or condition selected from the group consisting of sickle cell anemia, metabolic syndrome, thrombosis. The thrombosis may be venous thrombosis, deep vein thrombosis, portal vein thrombosis, renal vein thrombosis, arterial thrombosis, and post-surgical thrombotic complications arising from angioplasty and organ transplantation.

In certain aspects of the above methods, the compound is salicylamine. In other embodiments, the compound is selected from the following formula:

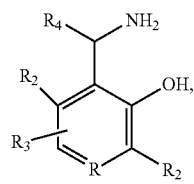

wherein: R is N or C; $R_2$ is independently H, substituted or unsubstituted alkyl; $R_3$ is H, halogen, alkoxy, hydroxyl, nitro; $R_4$ is H, substituted or unsubstituted alkyl, carboxyl; and pharmaceutically acceptable salts thereof.

In other embodiments, the compound is selected from the following formula:

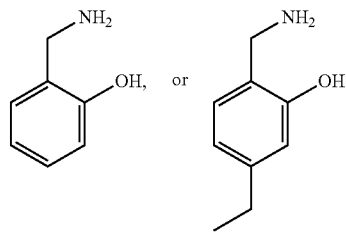

or a pharmaceutically acceptable salt thereof.

In other embodiments, the compound is selected from the following formula:

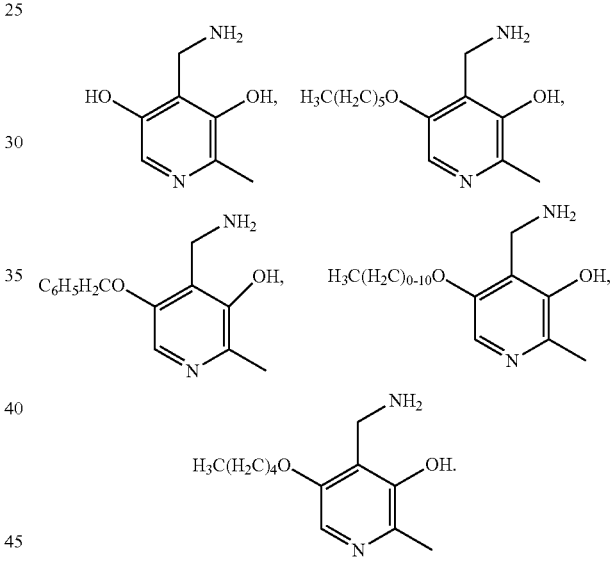

or a pharmaceutically acceptable salt thereof.

In other embodiments, the compound is selected from the following formula:

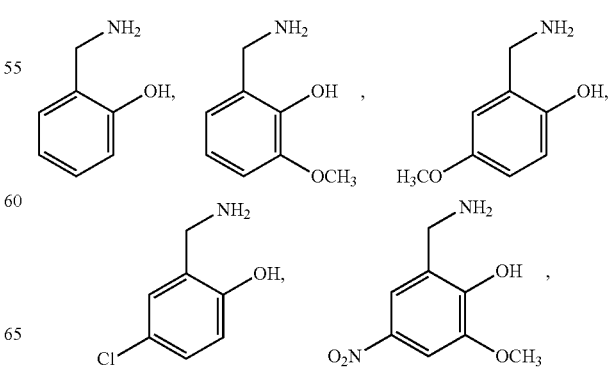

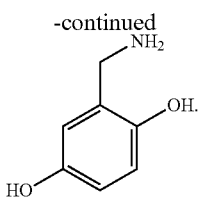

or a pharmaceutically acceptable salt thereof.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, pamoic, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The compounds of the present invention can be administered as the sole active pharmaceutical agent, or can be used in combination with one or more other agents useful for treating or preventing various complications, such as, for example, inflammation and other inflammation-related diseases. When administered as a combination, the therapeutic agents can be formulated as separate compositions that are given at the same time or different times, or the therapeutic agents can be given as a single composition.

As indicated herein, the compounds of the present invention may be made up in a solid form (including granules, powders or suppositories) or in a liquid form (e.g., solutions, suspensions, or emulsions). They may be applied in a variety of solutions and may be subjected to conventional pharmaceutical operations such as sterilization and/or may contain conventional adjuvants, such as preservatives, stabilizers, wetting agents, emulsifiers, buffers etc.

Thus, for administration, the compounds of the present invention are ordinarily combined with one or more adjuvants appropriate for the indicated route of administration. For example, they may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In therapeutic applications, the compounds of the present invention may be administered to a mammalian patient in an amount sufficient to reduce or inhibit the desired indication. Amounts effective for this use depend on factors including, but not limited to, the route of administration, the stage and severity of the indication, the general state of health of the mammal, and the judgment of the prescribing physician. The compounds of the present invention are safe and effective over a wide dosage range. However, it will be understood that the amounts of pyridoxamine actually administered will be determined by a physician, in the light of the above relevant circumstances.

Pharmaceutically acceptable acid addition salts of the compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., J. Pharmaceutical Science, 66: 1-19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Examples

The following example discusses MDA and dicarbonyl scavengers.

Activation of platelets signals cytosolic phospholipase $A_2\alpha$ activation, and an explosive release of arachidonic acid, which is metabolized by cyclooxygenase-1 (COX-1) to prostaglandin $H_2$ ($PGH_2$). In platelets, the thromboxane synthase enzyme catalyzes conversion of $PGH_2$ to both thromboxane $A_2$ and malondialdehyde (MDA) in approximately equimolar amounts (1).

MDA is an electrophile that reacts with amino groups, including the ε-amine of protein lysines. Reaction of MDA with lysine in vitro leads to formation of adducts with several structures (2, 3), including one that results from the reaction of this dicarbonyl with two lysines to produce intra- and inter-molecular crosslinks of macromolecules. Such crosslinks have been demonstrated when MDA is added to purified apoA-1 in vitro (2).

Without being bound by theory or mechanism, this evidence indicates that MDA is a major product of the thromboxane synthase and can modify protein structure in vitro indicates that platelet activation could lead to modification of platelet proteins by MDA.

Embodiments of the present invention demonstrate that activation of platelets ex vivo leads to thromboxane synthase-dependent MDA modification of platelet proteins. A stable isotope dilution method for analysis for the dilysyl-MDA crosslink utilizing liquid chromatography mass spectrometry (LC/MS/MS) has been developed, making it possible to demonstrate increased levels of MDA adducts of platelet proteins in diseases that are associated with increased platelet activation.

Methods

Chemicals and Reagents.

Ozagrel was from Cayman chemical Company (Ann Arbor, Mich.). TMP (precursor of MDA), arachidonic acid, sodium citrate, citric acid, lysine and aspirin (acetylsalicylic acid) were from Sigma-Aldrich (St. Louis, Mo.). Oasis™ HLB 1 cc cartridges containing 30 mg of poly(divinylbenzene-co-N-vinylpyrrolidone) copolymer, were obtained from Waters Corp. (Milford, Mass.). Lysine-[$^3$H, 99%] was from American Radiolabeled Chemicals, Inc. (ARC, St Louis, Mo.) and lysine-[$^{13}C_6$, 99%] was from Cambridge Isotope Laboratories, Inc. Salicylamine acetate (SA), 3-methoxysalicylamine acetate (3-MoSA), 5-ethylsalicylamine (EtSA), 5-methylsalicylamine (MeSA) and 4-hydroxybenzylamine (4-HoBA) were synthesized as previously described (4). Phosphate buffered saline (10×) was from Fisher BioReagents-Fisher Scientific (Fair Lawn, N.J.). Spin X centrifuge filters were purchased from Costar (Corning, N.Y.). The conjugated monoclonal antibodies anti-CD62p (P-selectin) and PE-conjugated anti-CD-41 were available from BD-Pharmingen (Franklin Lakes, N.J.). All solvents were HPLC-grade.

Equipment.

A scintillation counter (liquid scintillation analyzer) Tri-Carb 1900TR was from PerkinElmer. HPLC was performed using a Perkin Elmer Series 200 system (Perkin Elmer Shelton, Conn.) consisting of a system controller, a LC-pump, an autosampler, a column oven, a degasser and a UV-vis detector. The analytical Aquasil C18 reverse phase column (250×4.6 mm i.d.), from Thermo scientific Chromatography (Pittsburgh, Pa.) or a Phenomenex Kinetex 2.6 μM XB-C18 100A (75×2.1 mm i.d.), from Phenomenex, (Torrance Calif.) were used. A Liquid Chromatography (LC) system was connected to a Finnigan TSQ Quantum Triple Quadrupole mass spectrometer (Thermo Electron Inc., (San Jose, Calif.)) equipped with an electrospray source. LC/MS/MS Xcalibur software (version 1.3; ThermoFinnigan) was used to operate the instrument and to process the data. Aliquots of the samples were analyzed in the positive ion mode using an YMC™-ODS-AQ (250×2.0 mm, 5 μm particle size) column from YMC Co., Ltd, (Allentown, Pa.).

Figure 1:
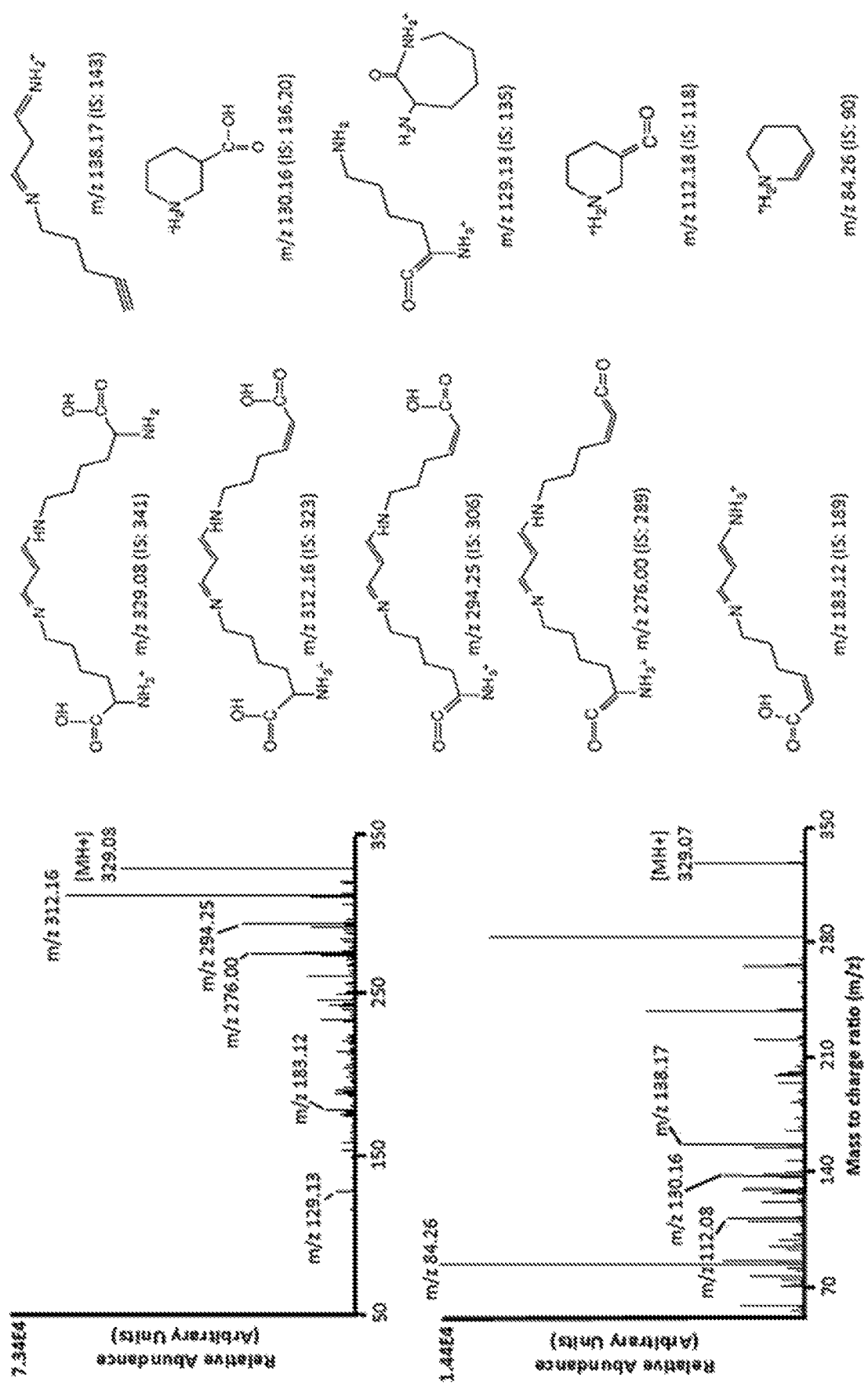
FIG. 1 shows LC/ESI/MS/MS spectra and selected ion monitoring of dilysyl-MDA crosslink, and structure of product ions. The [MH]+ ions of dilysyl-MDA crosslink (m/z 329) were subjected to CID. The product ions were scanned from m/z 50 to 350. The spectra recorded at −15 (upper spectrum) and −28 eV (lower spectrum) are shown with the proposed structures of the major fragment ions. The corresponding m/z for the internal standard (IS) are presented in parenthesis.

Dilysyl-MDA Crosslinks Adducts. For the characterization of dilysyl-MDA crosslinks, a mixture of [$^{12}$C] lysine or [$^{13}C_6$] lysine and TMP (ratio 3:2) was incubated in 1 N HCl for 2 h at 37° C. The reaction was then neutralized and let stand overnight at room temperature. The dilysyl-MDA crosslinks were purified initially with solid phase extraction (SPE) columns (Oasis HLB cartridge), preconditioned with 2 ml of methanol and 2 ml of water. The samples were loaded and then washed twice with 2 ml of water. The dilysyl-MDA crosslink were eluted with (1:1) methanol/ethyl acetate. The cartridge recovery was 99.83±16.58%. Under nitrogen, the residual product was concentrated down to 100 μl under nitrogen stream and analyzed by LC/MS/MS in the positive ion mode as described below. For determination of product ions, collision-induced dissociation of molecular ions of putative dilysyl-MDA crosslink was performed from −10 to −45 eV and scanning product ions from m/z 50 to 350. Spectra shown were obtained at −15 eV and −28 eV (FIG. 1).

Figure 2:
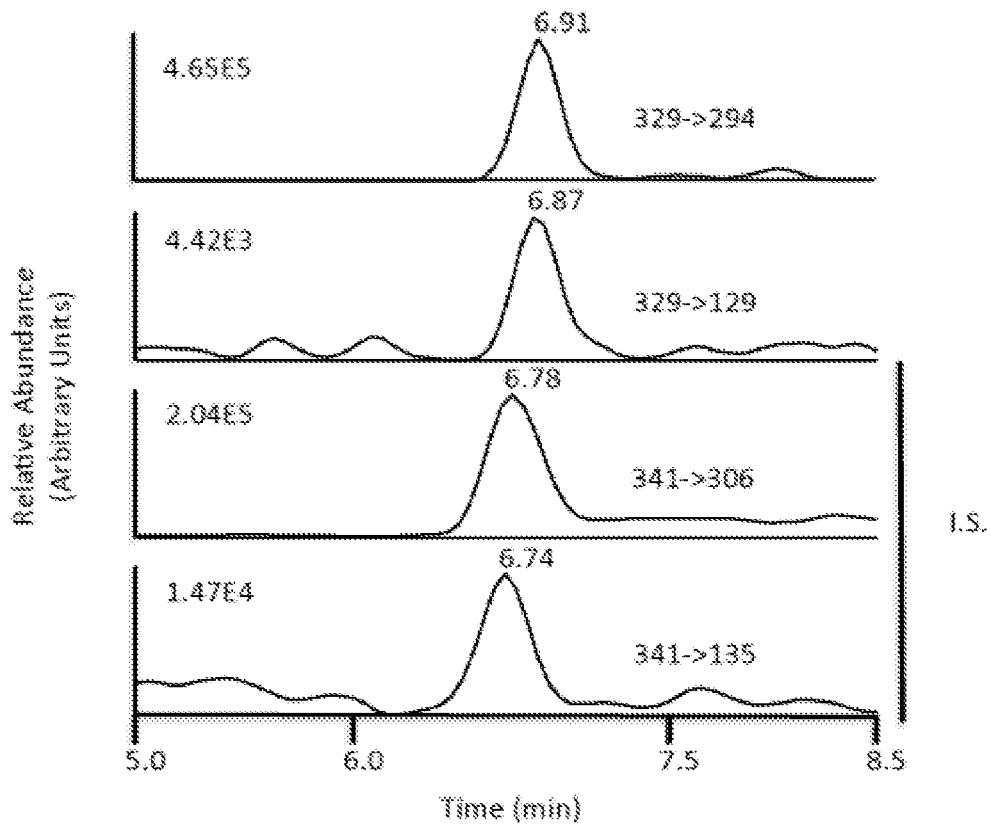
FIG. 2 shows typical SRM chromatograms of the dilysyl-MDA crosslink. Dilysyl-MDA crosslinks were purified by Oasis cartridge and HPLC, after being digested to single amino acid by step-digestion with proteases. The fractions containing the radioactivity were pooled, concentrated, and analyzed by LC/MS/MS. Selected reaction monitoring (SRM) of specific transition ions for the precursor ions at m/z 329 (upper panels) or m/z 341 (IS, lower panels), are shown. The IS was prepared from reaction of MDA with lysine and is assumed to be crosslinked to the α-amine, thus yielding a shorter retention time.

An internal standard of dilysyl-MDA crosslink (IS) was prepared as describe above by reaction of TMP in the presence of [$^{13}C_6$] lysine and [$^3$H] lysine. The dilysyl-MDA crosslinks was extracted as described previously and purified by HPLC. Fractions were collected every 0.5 min and presence of radioactivity was determined using a scintillation counter. The fractions containing radioactive dilysyl-MDA crosslinks ([$^3$H] lysine tracer in internal standard) were combined and analyzed by LC/MS/MS. To achieve a higher peak intensity and better peak shape, optimization was done using a gradient of acetonitrile/water with an addition of 0.1% formic acid to the mobile phase. The development of the chromatographic system was focused on shortening retention times while preserving the chromatographic separation of the analytes from the matrix contaminants. This was achieved by using a flow rate of 0.2 ml/min with the gradient described in the Methods section. These ions had an acceptable retention time (6.9 min and 6.7 min, respectively; FIG. 2). The overall analysis time was 18 min including re-equilibration time for the column with the initial mobile phase.

The radioactivity of the solution was counted using a scintillation counter and the concentration was calculated from the specific activity of the [$^3$H] lysine. The dilysyl-MDA crosslink is stable: 99.23% was recovered after storage up to 9 months at −80'C.

Method Validation Procedure.

Quality Control (QC) samples were prepared from washed platelets obtained from aphorised platelet units obtained from the Vanderbilt Blood bank. Aliquots of 3 mg of protein and all stock of dilysyl-MDA crosslink standard were stored at −80° C. until used. The stability of dilysyl-MDA crosslinks was assessed by analyzing samples stored at −80° C. for up to 9 months. Carry over was evaluated by placing vials of blank solvent at several locations in the analysis set. Specificity and selectivity of the assay were assessed by comparing un-activated washed platelet samples to washed platelet samples activated with 5 µM arachidonic acid for 2 h.

To determine the overall recovery of the cartridge, digested QC sample was spiked with IS before or after SPE. The samples were purified and analyzed. The peak areas obtained in neat solution standards as A, the corresponding peak areas for post-extraction spiked samples as B, and the peak areas for extracted samples as C, were used to calculated the IIS (ionization suppression) and AE (absolute recovery) values as follow: HS (%)=B/A×100%; AE (%)=C/B×100% (n=3). The variability of the digestion was assessed by comparing the amount of dilysyl-MDA crosslinks, in samples split before or after digestion, and it was determined according to the following equation: (% digestion=(amount of crosslinks in sample digested after split/amount of crosslinks in sample digested before split)×100.

In order to assess the intra- and inter-batch precision and accuracy of the assay, QC samples at 1.5, 2.1, 5.8 and 12.5 mg were analyzed. The intra-batch precision (repeatability) of the assay was evaluated by the relative standard deviation (% RSD) of three replicates and the inter-batch precision (reproducibility) was evaluated by the analysis of standard curve samples in three batches (in duplicate); % RSD=(SD/mean)×100. The assay was considered to be acceptable if % RSD<15%.

To determine the linearity of the assay, we prepared 1.8 mM stock solution of dilysyl-MDA crosslink in water containing 0.1% formic acid. A dose-response curve ranging from 0.008 pg to 7.5 pg was prepared by weighing different amounts of synthetic dilysyl-MDA crosslink, and the area under the curve (AUC) was recorded by LC/MS/MS as described in Methods section. Increasing amounts of dilysyl-MDA crosslinks gave a linear response with y=3.19e+006 x+442297, where y is the measured AUC of dilysyl-MDA crosslink and x is the weighed dilysyl-MDA crosslink in pg. The 1/slope and the correlation coefficient ($r^2$) of the calibration plot were 3.12e-007 and 0.93, respectively.

The limit of quantification (LOQ) and limit of detection (LOD) were calculated directly from the calibration plot. The calibration sample was prepared with [$^{12}$C] lysine, trace of [$^3$H] lysine and TMP. The reaction mixture was extracted by SPE as previously described in the section of the preparation of dilysyl-MDA Crosslink standard. The responses AUC (area under curve) of the selected fragment relative to the corresponding amount of adduct (in pg) were used to construct standard curves by least square linear regression analysis. LOQ and LOD were calculated as 10σ/S and 3.3σ/S, respectively, where a is the standard deviation of y-intercept of regression equation and S is the slope of the calibration plot (5).

Sample Collection.

Written informed consent was obtained from study participants and human blood was obtained following a protocol approved by the Institutional Review Board of Vanderbilt University. Samples were obtained from three different populations: healthy subjects who had no component of the MetSyn or SCD, patients with MetSyn and patients with SCD. Patients with MetSyn were 35-75 year old and fit the MetSyn criteria in accord with the American Heart Association/National Heart, Lung, and Blood Institute criteria (6). Patients with SCD were 25-50 year old and were homozygous sickle (SS) or compound heterozygote with beta-thalassemia (Sβ-thal) phenotype. All recruited patients were queried about their NSAID use and enrolled only if they could confirm lack of NSAIDs use for at least 7 days prior to sample collection.

Preparation of Washed Platelets.

Washed platelets were prepared following two different protocols depending on whether they were used for the in vitro studies of the mechanism by which MDA adducts are generated, or for the in vivo measurements of Protease-Derived Lysyl-MDA-Lysyl crosslink (dilysyl-MDA crosslink) levels as a marker of platelet activation. The two protocols are described below.

In Vitro Platelet Activation:

Blood obtained from healthy volunteers was collected into vacuum tubes containing citrate, from a peripheral vein using a 21-gauge needle, and washed platelets were prepared as previously described (7). The platelets were counted with a Coulter counter and diluted with resuspension buffer to a final concentration of 300,000 platelets/µl, and aliquoted in volumes corresponding to 500 µl. The aliquots were preincubated for 40 min at room temperature with vehicle, the thromboxane synthase inhibitor ozagrel (100 µM), aspirin (100 µM) or the MDA scavengers, SA (1.5 mM) or 3-MoSA (1.5 mM). Next, arachidonic acid (5 µM) was added and the platelets were incubated for an additional 2 h at room temperature. The reactions were stopped by adding indomethacin (100 µM) and the aldehyde scavenger pyridoxamine (1 mM) for 30 min at 4° C., to inhibit all residual COX-1 activity and to prevent formation of MDA adducts on proteins during the purification process, respectively. An aliquot (5 µl) of sample was used for protein estimations using a BCA assay.

In vivo platelet activation: Metabolic Syndrome and Sickle Cell patients. Formation of MDA adducts on platelet proteins during platelet activation in vitro suggested the hypothesis that MDA-protein adducts in platelets would be elevated in states of chronic platelet activation in vivo. Because most proteins in the anuclear platelet exhibit very little turnover, covalent adducts of these proteins would be expected to accumulate in states of ongoing platelet activation. Accordingly, the levels of dilysyl-MDA crosslinks in platelets were measured in two conditions in which there is evidence of in vivo platelet activation, metabolic syndrome (MetSyn) (8, 9) and sickle cell disease (SCD) (8, 9), and compared to the levels in platelets from healthy subjects isolated from blood collected in the same conditions.

Blood was collected into a 5 ml syringe containing 0.4% sodium citrate, aspirin (100 µM), apyrase (2 Units), carbaprostacyclin (1 µM), and SQ 29,548 (10 nM) final concentration (to prevent ex vivo platelet activation). The blood was incubated at room temperature for 40 min prior to preparation of washed platelets and protein quantification, which was performed as described above. In all instances, two aliquots of washed platelets from the quality control (QC) were processed in parallel. Indomethacin (100 µM) and pyridoxamine (1 mM) were added prior protein digestion as described above.

Preparation of QC Samples from Washed Platelets.

Human platelet concentrate obtained from the Blood Bank at Vanderbilt University Hospital was acidified to pH 6.4 with 0.15 M citric acid. Pyridoxamine (1 mM final concentration) and indomethacin (100 µM final concentration) were added to the concentrate and incubated for 30 min at room temperature.

Platelets were then centrifuged at 1,000 g for 10 min. The pellet was resuspended in suspension buffer (8.3 mM sodium phosphate, pH 6.5, 0.109 M NaCl, and 5.5 mM glucose) at final concentration of 600,000 cells/μl, and 100 μl aliquots (2.5 mg of protein) were stored at −80° C. until used.

Analysis of Protease-Derived Lysyl-MDA-Lysyl Crosslinks (Dilysyl-MDA Crosslinks) in Washed Platelets by LC/ESI/MS/MS.

Samples (around 3 mg of protein) were digested with proteases as previously described for lysyl-lactam adducts (7). In summary, the samples were subsequently heated at 95° C. and allowed to cool at room temperature, before step digestion with pronase (1 mg) at 37° C. for 24 h. Pronase was inactivated by heating samples at 95° C. for 10 min and then cooled to room temperature. Then, 1 μl of 500 mM aminopeptidase was added for every 1 mg of sample protein and incubated at 37° C. for 24 h. Five nanograms of $^{13}C_6$-dilysyl-MDA crosslink standard were added to each platelet sample and dilysyl-MDA crosslinks were purified using Oasis cartridge as described above in the section for the preparation of dilysyl-MDA Crosslink standard. The eluate was dried under nitrogen flow to a volume of 100 μl, diluted up to 1 ml with a 0.1% formic acid aqueous solution, and filtered using a 0.22 μm nylon Spin-x centrifuge tube spun at 6,000 rpm for 5 min. Samples were purified by HPLC through the Thermo Scientific Aquasil C18 column. The fractions containing the radioactivity were pooled, concentrated in Oasis HLB cartridge, and then dried under nitrogen to a final volume of 40 μl.

Pooled HPLC fractions concentrated using Oasis were analyzed by LC/MS/MS using an YMC OD-AQ column. Solvent A (99.9% $H_2O$/0.1% formic acid) and solvent B (99.9% ACN/0.1% formic acid) were filtered through a 0.45-μm filter prior to mixing and ultrasonically degassed after mixing. The gradient was as follows: 0-5 min 100-0% A, 5-7 min 0% A, 7-9 min 0-100% A, 9-15 min 100% A, with a flow rate of 0.2 ml/min. The mass spectrometer was operated in the positive ion mode and the electrospray needle was maintained at 4000 V. Nitrogen was used for both the sheath and auxiliary gas at pressures of 30 and 5 arbitrary units, respectively. The optimizing skimmer offset was set at 10, capillary temperature was 300° C. and the tube lens voltage was 195 V. Selected reaction monitoring of specific transition ions for the precursor ions at m/z 329→294 (dilysyl-MDA crosslink) or m/z 341→306 (IS) at −15 eV were used. These settings were used during all experiments, including the validation procedure.

An SRM chromatogram of dilysyl-MDA crosslinks from a representative experiment evaluating the effect of platelet activation on formation of the crosslinks is depicted in FIG. 2, and this demonstrates that no interfering peaks from endogenous compounds were observed at the retention times for either the dilysyl-MDA crosslink or IS, demonstrating that our purification method removes potentially interfering endogenous compounds and that the observed signals are specific for the analytes.

Synthesis of Scavenger-MDA Adducts.

A mixture of SA or 3-MoSA and TMP (0.1 mmol each) was incubated in 1 N HCl (1 ml) for 2 h, at 37° C. The reaction was then neutralized with 10 N NaOH and incubated overnight at room temperature. The scavenger-MDA adducts were extracted three times with 500 μl of ethyl acetate. The extracts were pooled and dried down under nitrogen stream, resuspended in 100 μl of ACN-water (1:1, v/v), vortexed, and filtered through a 0.22-um spinxcolumn. The scavenger-MDA adducts were analyzed by direct infusion on the TSQ Quantum triple quadrupole mass spectrometer equipped with a standard electrospray ionization source.

On a larger scale, TMP (0.84 ml, 5 mmol) was stirred with 1 N HCl (10 ml) at room temperature and diluted with water (90 ml). It was neutralized with $K_2HPO_4$ (7 g) and treated with SA (0.9 g, 5 mmol) or MoSA (1.06 g, 5 mmol) for 4h. The adduct was extracted with ethyl acetate (4×20 ml). After removal of solvents, the adduct was purified on a column of silica with ethyl acetate as eluent; yield 30%.

Determination of the Rate of Reactivity of the Scavengers with MDA In Vitro.

$N^\alpha$-Acetyllysine with or without SA, 3-MoSA or 4-HoBA was incubated at 37° C. in the presence of MDA (ratio 1:1) in 0.1 M phosphate, pH 7.4. After 4 h, 10 μl aliquots were diluted to 200 μl with solvent A and analyzed by HPLC. Solvent A consisted to 20% methanol/0.2% formic acid and solvent B was 99.8% methanol/0.2% formic acid. The gradient was as follows: 0-1 min 100% A, 1-7 min 100-0% A, 7-14 min 0% B. Phenomenex Kinetex column at a flow rate of 0.2 ml/min and the absorbance at 280 nm were used.

LC/MS/MS Quantification of Scavengers-MDA Adducts from Washed Platelet.

Washed platelets were activated as described above in the section "ex vivo activation". The scavenger-MDA adducts were extracted three times with 500 μl of ethyl acetate from 50 μl of the reaction mixture, as described above. The extract was dried down, re-suspended in 100 μl of ACN-water (1:1, v/v), vortexed, and filtered through a 0.22-um spinxcolumn. The reactions were analyzed by LC/MS/MS using the column and gradient as described above. The mass spectrometer was operated in the positive ion mode and the spray voltage was maintained at 5000 V. Nitrogen was used for the sheath gas and auxiliary gas at pressures of 30 and 5 arbitrary units, respectively. The optimized skimmer offset was set at 10, capillary temperature was 300° C. and the tube lens voltage for both compounds was set to 49. Selected reaction monitoring of specific transition ions for the precursor ions at m/z 178→106 (SA-MDA adduct) or m/z 208→136 (3-MoSA-MDA adduct) at −15 eV were used.

GC/NICI/MS Quantification of Thromboxane $B_2$.

Serum $TxB_2$ ($sTxB2$) was measured as an indicator of inhibition of platelet COX activity from blood drawn into non-citrated vacuum tubes. Serum from patients was prepared by incubating the blood at 37° C. for 45 min and then centrifuged at 3,200×g for 15 min. Serum was separated and stored at −80° C. until analysis. For ex vivo experiment, 50 μl of washed platelets were used. sTxB2 was assayed by stable isotope dilution gas chromatography/mass spectrometry (GC/MS) with selective ion monitoring as described previously (10).

Analysis of P-Selectin Expression.

An aliquot of citrated blood (10 μl) was added to 980 μl of PBS containing PE-conjugated 10 μl anti-CD-41a antibody and 10 μl APC-conjugated anti-P-selectin antibody (CD62P), then incubated for 30 min at room temperature in the dark. At this time, platelets were fixed by adding 100 μl of 2% formaldehyde in PBS for 45 min, and analyzed by flow cytometry as described below.

Analysis of Reticulated Platelets.

Reticulated platelets were characterized by measuring platelets positive for staining with thiazole orange following a method described by Koike et al. (11) and modified as follows. A PE-conjugated anti-CD-41 an antibody (BD-Pharmingen) (10 μl) was added to 980 d of PBS containing thiazole orange at 100 ng/ml. An aliquot of whole blood (10 μl) was added to this tube, incubated for 30 min at room temperature in the dark, and platelets were fixed by adding 100 µl of 2% formaldehyde in PBS, for 45 min. The platelets were then analyzed by flow cytometry as described below.

Flow Cytometry Analysis.

Expression of markers of platelet activation were performed by flow cytometry analysis as described by Faull et al. (12). Single color staining controls were included in each assay to facilitate proper fluorescence compensation. Samples were analyzed on a FACS canto II (BD biosciences) (13). Increase in mean fluorescence intensity and % positive cells was recorded. Each time point and dose were compared to an unstimulated control and data was expressed as the fold increases over unstimulated conditions or as the absolute values according to the experimental design.

Statistical Methods.

Statistical analysis was performed using GraphPad Prism 4.0 (GraphPad Software, Inc., San Diego, Calif.). Data are expressed as mean±SEM, unless specified otherwise. The statistical significance was determined using One-way ANOVA (Tukey's Multiple Comparison Test) or t-test (two-tailed) with Welch's correction.

Results

Formation and Characterization of Dilysyl-MDA Crosslinks.

The present inventors examined the different adducts formed by the reaction of the amino acid, lysine, with MDA derived from tetramethoxypropane (TMP), a MDA precursor, using full scan mass spectrometry. Three major covalent adducts were identified: (i) $N^\varepsilon$-propenal-lysine (m/z 201), (ii) dihydropyridine (DHP)-lysine (m/z 281) and (iii) the N,N'-disubstituted 1-amino-3-iminopropenal cross-link formed by reaction of MDA with two lysines (dilysyl-MDA crosslink; m/z 329). Because both the M-propenal-lysine and the DHP-lysine adducts still contain aldehyde moieties, they can further react with free amines during sample processing. The present inventors analyzed the DHP lysyl adduct by mass spectrometry before and after incubation with the aldehyde scavenger, pyridoxamine. The data show that the DHP lysyl adduct still reacts with free amines, causing its disappearance and the concomitant appearance of the dipyridoxamine adduct, making them unsuitable for quantitation. In contrast, the dilysyl-MDA crosslink is no longer reactive and thus was chosen for quantification.

The full mass spectra for the dilysyl-MDA crosslink and its internal standard (IS) adduct revealed predominant peaks at m/z 329 and m/z 341 respectively as protonated molecular ions ([M+H]$^+$) in LC/MS/MS. These precursor ions were fragmented and the product ion spectra were obtained. The corresponding fragments in the CID spectra obtained at −15 eV and −28 eV is shown in FIG. 1. The probable cleavage reactions of dilysyl-MDA crosslink (m/z 329) are presented in FIG. 1. The ion fragment at m/z 312, corresponding to the deaminated dilysyl-MDA crosslink is seen at relatively low voltages, followed by dehydration to produce m/z 294. A second dehydration from m/z 294 will produce the product ion m/z 276. The ion m/z 183 corresponds to the loss of one lysine from m/z 294, while m/z 129 is the cyclization of the lysine fragment (FIG. 1). The fragmentation of the IS (at m/z 341) are indicated in parenthesis (FIG. 1).

To ascertain that the fragmentation pattern observed for the dilysyl-MDA crosslink is different from the other MDA adduct structures, we purified both the NE-propenal-lysine and the DHP-lysine adducts and analyzed them by LC/ESI/MS/MS.

Selected reaction monitoring (SRM) chromatograms for the transitions of m/z 329 to m/z 294 and 129 (dilysyl-MDA crosslinks), and the transitions of m/z 341 to m/z 306 and 135 ([$^{13}C_{12}$] dilysyl-MDA crosslinks IS) are shown in FIG. 2. The fragment ions of the [$^{13}C_{12}$] dilysyl-MDA crosslink internal standard elute at a similar but slightly earlier time than the unlabeled dilysyl-MDA-crosslink. The use of an initial solid phase extraction cartridge followed by High Pressure Liquid Chromatographic (HPLC) purification minimized impurities in the sample extracts that could produce ion suppression of the target analytes. The use of SRM provided high selectivity, sensitivity and intensity for both dilysyl-MDA crosslink and IS.

Validation of LC/MS/MS Method to Measure Dilysyl-MDA Crosslink.

Assays were validated according to the U.S. FDA guidance on bioanalytical method validation (5). The measured area under the SRM curve for the dilysyl-MDA crosslink was linear with the amount of weighed dilysyl-MDA crosslink added to the assay. The limit of detection (LOD) and limit of quantification (LOQ) were 2.1 pg and 7.1 pg, (S/N>3). These low values are indicative of the high sensitivity of the method. The overall variability of the digestion steps was 4.0%. The intra- and inter-day precisions were acceptable with relative standard deviation of 6.7 and 6.6% respectively suggesting that the method is reproducible for quantification of dilysyl-MDA crosslink in washed platelets.

Platelet Activation Leads to Modification of Platelet Proteins by MDA.

Figure 3:
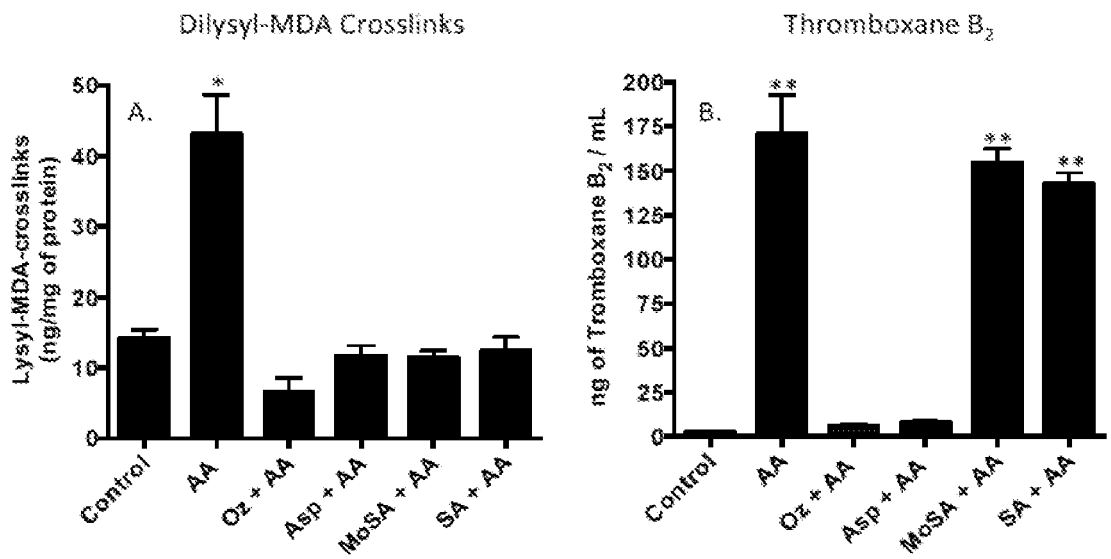
FIG. 3 is a graph that shows dilysyl-MDA crosslinks are formed in activated human washed platelets in a thromboxane synthase-dependent way. Human washed platelets were preincubated with vehicle (subject) or either with 100 µM Ozagrel, 100 µM Aspirin or 1.5 mM SA or 3-MoSA for 40 min. After incubation, 5 µM arachidonic acid was added for 2 h. (A) Dilysyl-MDA crosslinks were purified and quantified by isotopic dilution using LC/MS/MS. The product ions at m/z 294 for dilysyl-MDA crosslink and m/z 306 for the IS were monitored. *p<0.0001 vs all other conditions. (B) As a measure of COX activity, $TxB_2$ was determined by GC/MS from 50 µl of washed platelet. **p<0.0001 vs subject, Oz or ASA. One-way ANOVA followed by Tukey's multiple comparisons test was used. (n>6).

To determine whether platelet activation leads to modification of platelet proteins by MDA, we compared the level of protease-derived dilysyl-MDA crosslinks in unactivated washed platelets with washed platelets activated with 5 µM arachidonic acid for 2 h. Dilysyl-MDA crosslinks increased from a mean of 14.2 (SE±1.2) to 43.1 (SE±5.6) following platelet activation (p<0.0001) (FIG. 3). To assess whether the crosslinks come from proteins or from the pool of lysine available in platelets, we compared the levels of dilysyl-MDA crosslinks from samples digested to single amino acids to those of samples where the last protease (aminopeptidase) was omitted. Our data showed that 91% of the crosslinks are derived from adducted proteins.

Inhibitors of Thromboxane Synthesis and Scavengers of Reactive Dicarbonyls Protect Proteins from Adduction by MDA in Activated Platelets.

MDA can be synthesized in platelets by sequential metabolism of arachidonic via COX-1 followed by the thromboxane synthase (1). To ascertain that dilysyl-MDA crosslinks were formed during ex vivo platelet activation via the COX-1-initiated thromboxane pathway, human washed platelets were preincubated with vehicle, the COX-1 inhibitor aspirin or the thromboxane synthase inhibitor ozagrel prior addition of 5 µM arachidonic. Both aspirin and ozagrel reduced levels of the dilysysl-MDA crosslink to baseline levels (FIG. 3A). Together, these data demonstrate that MDA is generated in human platelets in a COX-1/thromboxane synthase-dependent fashion and forms covalent adducts with proteins.

The present inventors have previously developed small molecules that react with the 7-ketoaldehyde levuglandins 3 orders of magnitude faster than with lysine, and shown that these "scavengers" protect proteins from covalent adduction by these 1,4-dicarbonyls (4). They now find that these scavengers also protect proteins from covalent modifications by the 1,3-dicarbonyl, MDA. Human washed platelets were pre-incubated with the scavengers, salicylamine (SA) or 3-methoxysalicylamine (3-MoSA), prior to activation with arachidonic acid. The data show that SA and 3-MoSA decreased levels of dilysysl-MDA crosslinks to baseline levels (FIG. 3A), demonstrating that the scavengers are efficient in protecting proteins from adduction by MDA. The present inventors further evaluated the efficacy of other SA analogs to protect protein against adduction by MDA and found that 5-ethylsalicylamine (EtSA) and 5-methylsalicylamine (MeSA) were as effective as scavengers as was SA.

To exclude the possibility that the scavengers reduced MDA adducts by inhibiting COX-1, the level of thromboxane $B_2$ ($TxB_2$) following platelet incubation with scavengers was measured. In contrast to aspirin or ozagrel, which both inhibited $TxB_2$ levels by 96%, neither SA nor 3-MoSA significantly affected $TxB_2$ levels (FIG. 3B), demonstrating that the reduced formation of protein adducts by these compounds is due to direct scavenging of MDA and not by inhibiting COX-1.

Characterization of the Product of Reaction of Scavengers with MDA.

It was hypothesized that the scavengers prevent formation of MDA-lysine adducts by preferential formation of stable MDA-scavenger adducts, and that the greater reactivity of the scavengers with MDA results from the presence of 2-hydroxyl in SA and its analogues. The products of the reaction of SA and 3-MoSA with MDA were characterized by LC/MS/MS as the N-propenal adducts of the scavengers. The structures of N-propenal-3-MoSA and N-propenal-SA adduct were confirmed by NMR. The data show that the propenal adducts are stabilized by a hydrogen bond between the carbonyl of MDA and the 2-hydroxyl group on the ring.

Figure 4:
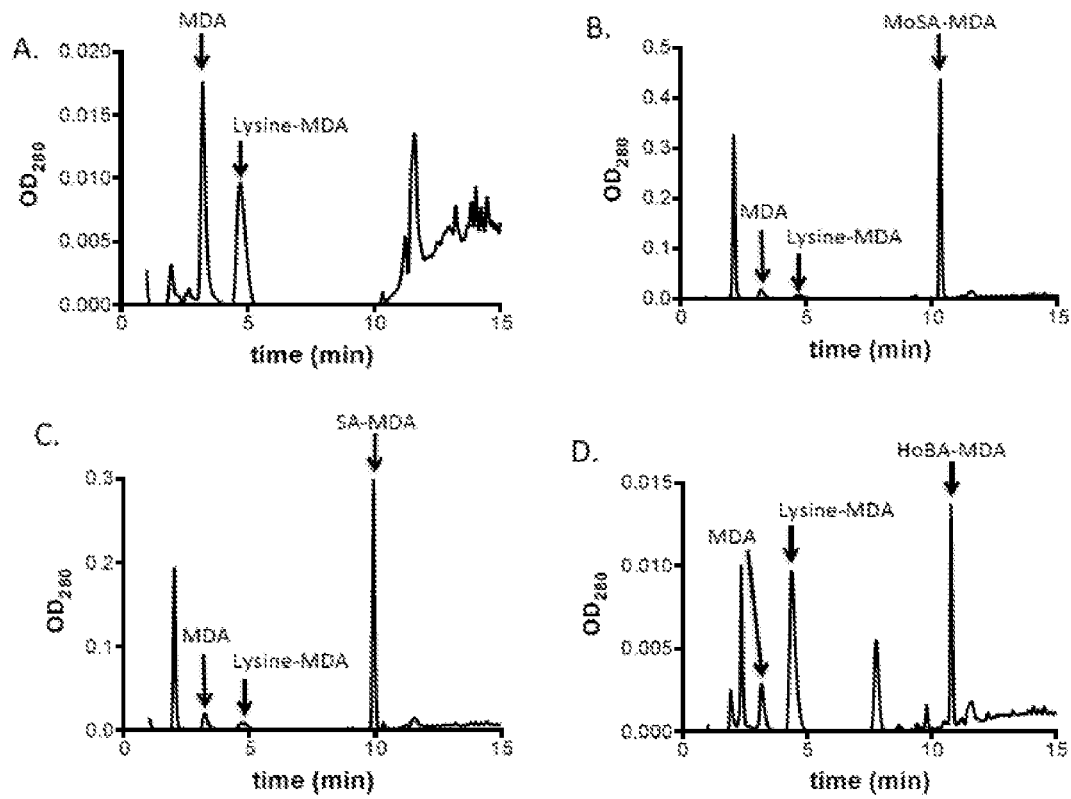
FIG. 4 are graphs that show lysine-MDA adducts formation is inhibited by SA or MoSA. Lysine and MDA were incubated at 37° C. for 4 h in presence of vehicle (A), MoSA (B), SA (C) or 4-HoBA (D). The profiles were determined by HPLC as described in Methods section.

The formation of MDA adducts of the scavengers was compared with that of MDA adducts of lysine, employing analysis of the products on HPLC (FIG. 4). Formation of the MDA adduct of 3-MoSA was 15.1 fold greater than that of the MDA-lysine adduct, and the formation of the MDA adduct of SA was 9.2 fold greater than that of the lysine adduct, indicating the strong preferential reactivity of MDA with these 2-hydroxy-benzylamine scavengers. By contrast, 4-hydroxy-benzylamine (4-HoBA) formed an MDA adduct in an amount even less than that of lysine (0.6 fold).

The hydrogen bonding of MDA with the 2-hydroxyl of the scavengers likely facilitates the interaction of MDA with the amino group that initiates formation of the adduct, accounting for the preferential reactivity of MDA with the scavengers relative to reaction with the amino group of lysine. By contrast, the 4-hydroxyl of 4-HoBA is unable to participate in H-bonding with MDA, likely due to its remoteness from the amine.

Levels of Scavenger-MDA Adducts in Human Washed Platelets.

Figure 5:
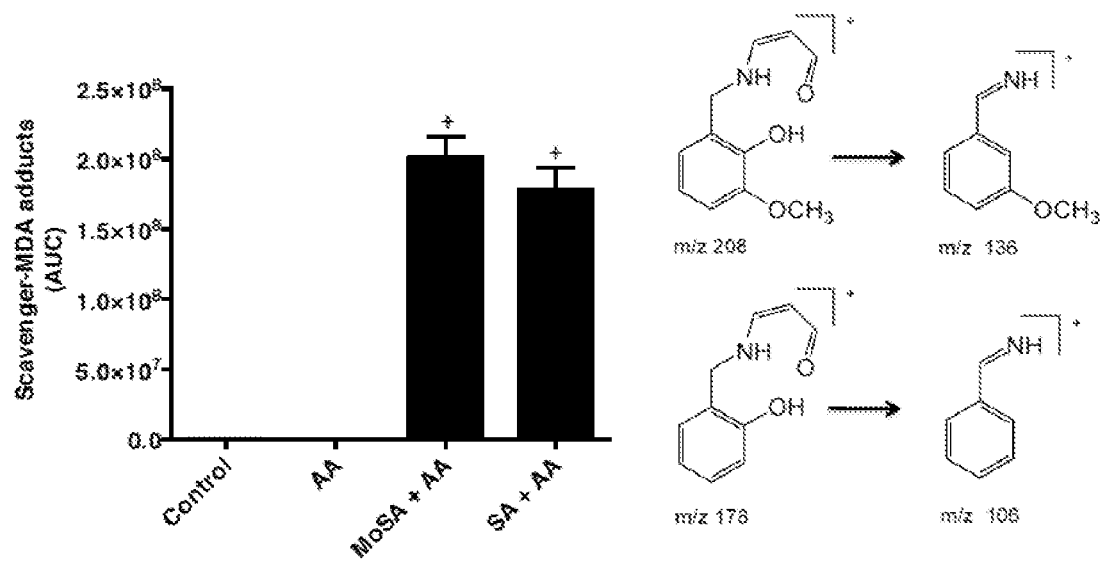
FIG. 5 is a graph that shows scavenger-MDA adducts are formed when human washed platelets are activated in presence of scavengers. Human washed platelets were preincubated with MoSA or SA (1.5 mM final concentration)

The formation of MDA adducts of SA and 3-MoSA in activated platelets was analyzed. The adducts were extracted from the platelet supernatant and analyzed by LC/MS/MS by monitoring the transitions of m/z=208 to m/z=136 and m/z=178 to m/z=106 for 3-MoSA-MDA and SA-MDA, respectively (FIG. 5). We find that inhibition of dilysyl-MDA crosslinks on platelet proteins is associated with the concomitant appearance of the equivalent scavenger-MDA adduct (FIG. 5). These results demonstrate that the protective effect of the scavengers is due to its reaction with MDA and formation of a stable non-reactive adduct.

Increased Formation of MDA Adducts of Platelet Proteins In Vivo in Patients with Metabolic Syndrome (MetSyn).

Analysis of dilysyl-MDA crosslinks of platelet proteins provided significant discrimination between the group of patients with MetSyn and healthy subjects. Levels of dilysyl-MDA crosslinks in the platelets of patients with MetSyn were increased 2-fold in comparison with those of healthy subjects (MetSyn: 6.63±3.56 ng/mg protein; healthy subjects 3.38±1.43 ng/mg; p=0.0002) (FIG. 6A). 55% of the patients had values elevated above the normal range. The capacity of platelets to produce thromboxane $A_2$ ex vivo was not different between patients with MetSyn and healthy subjects (serum $TxB_2$ was 265.2±74.6 ng/ml in patients with MetSyn and 278.1±114.2 ng/ml in healthy subjects).

The increases in dilysyl-MDA crosslinks were compared with those of single platelet P-selectin expression, a marker of in vivo platelet activation. Single platelet levels of P-selectin were increased significantly but to a lesser extent (1.3 fold); levels in MetSyn were 4.73±2.06% and healthy subjects 3.66±0.89% (p=0.0002), with values above the upper limit of normal in 37.5% of patients. Levels of reticulated platelets, indicators of platelet turnover, were only 1.2 fold increased in MetSyn (2.18±1.55%, when compared to healthy subjects (1.85±1.18%) and the difference was not significant.

Increased formation of MDA adducts of platelet proteins in vivo in patients with Sickle cell disease. The levels of dilysyl-MDA crosslinks in protein from platelets of patients with SCD (6.52±2.67 ng/mg of protein) were 2-fold higher than those of healthy subjects (3.38±1.43 ng/mg of protein; p<0.0001) (FIG. 6B). When patients were treated with the non-selective cyclooxygenase inhibitor, ketorolac, during admission for vaso-occlusive crisis, the levels of platelet dilysyl-MDA crosslinks were significantly lower (3.15±1.18 ng/mg of protein), consistent with inhibition of the biosynthesis of MDA that is derived from COX-1. Verifying the inhibition of platelet COX1 by ketorolac, levels of serum $TxB_2$ during ketorolac treatment were reduced from 219.7±183.1 ng/mL to 68.9±127.7 ng/mL.

This Example demonstrates nuclear penetration of an embodiment of the present invention.

FIGS. 7 and 8 show that embodiments of the present invention are active in platelets, but that inhibition of LG adducts in the nucleus is a more selective process. Thus, 3-MOSA, which is active in the platelet is inactive in the nucleus as reflected by its lack of effect on LG adducts of histones. Pentylpyridoxamine which is an effective scavenger in the platelet is only partially effective in the nucleus. On the other hand, 5-ethylsalicylamine is an effective scavenger in the nucleus. It can be concluded that there is good penetration of the scavenger into cells, but their access to the nuclear compartment is more selective. It is the finding that 5-ethylsalicylamine is a nuclear penetrant scavenger that is novel. No investigator has reported on the nuclear penetration of any scavenger heretofore, and it is this finding of selective nuclear uptake that is new and is the basis for considering that 5-ethylsalicylamine is an agent that can protect histones and DNA from reactive dicarbonyls.

FIG. 7 shows inhibition of formation of LG adducts in platelets. Human platelets were pre-incubated with 10 μM dazoxiben, a thromboxane synthase inhibitor, and 1 mM of the specified compound or vehicle (control) for 30 min. After incubation, 20 mM arachidonic acid was added for 2 h, and then the proteins were precipitated and digested to single amino acids by step-digestion with proteases. The daughter ions at m/z 332.1 and 84.1 for the lactam were monitored. Values are means±SD (n=9) *P<0.001 vs. control, +P<0.001 vs. 100 μM concentration.

FIG. 8 shows that an embodiment of the present invention, EtSA, blocks LG-lysyl adduct formation on histones. (A). Scavengers were screened in RAW264.7 cells for the ability to decrease LG adduct formation on histones. Scavengers used were glucosamine (GA), 3-methoxysalicylamine (3-MoSA), pentylpyridoxamine (PPM), and 5-ethylsalicylamine (EtSA). Cells were stimulated to express COX-2, pretreated 45 min. with 500 μM scavenger or vehicle ($H_2O$), and given 20 μM AA for 1 h before lysing and extracting histones. Histone proteins were analyzed by LC/ESI/MS/MS for LG-lysyl lactam adduct, n=2.

REFERENCES

1. Hecker, M., M. Haurand, V. Ullrich, U. Diczfalusy, and S. Hammarstrom. 1987. Products, kinetics, and substrate specificity of homogeneous thromboxane synthase from human platelets: development of a novel enzyme assay. *Arch Biochem Biophys* 254: 124-135.
2. Shao, B., S. Pennathur, I. Pagani, M. N. Oda, J. L. Witztum, J. F. Oram, and J. W. Heinecke. 2010. Modifying apolipoprotein A-I by malondialdehyde, but not by an array of other reactive carbonyls, blocks cholesterol efflux by the ABCA1 pathway. *J. Biol. Chem.* 285: 18473-18484.
3. Uchida, K. 2000. Role of reactive aldehyde in cardiovascular diseases. *Free Radic Biol Med* 28: 1685-1696.
4. Zagol-Ikapitte, I., V. Amarnath, M. Bala, L. J. Roberts, 2nd, J. A. Oates, and O. Boutaud. 2010. Characterization of scavengers of gamma-ketoaldehydes that do not inhibit prostaglandin biosynthesis. *Chem. Res. Toxicol.* 23: 240-250.
5. US Department of Health and Human Services, F. a. D. A., Center for Drug Evaluation and Research, Center for Veterinary Medicine. 2001. US DHHS, FAD, CDER. Guidance for Industry: Bioanalytical Method Validation.
6. Grundy, S. M., J. I. Cleeman, S. R. Daniels, K. A. Donato, R. H. Eckel, B. A. Franklin, D. J. Gordon, R. M. Krauss, P. J. Savage, S. C. Smith, Jr., J. A. Spertus, F. Costa, A. American Heart, L. National Heart, and I. Blood. 2005. Diagnosis and management of the metabolic syndrome: an American Heart Association/National Heart, Lung, and Blood Institute Scientific Statement. *Circulation* 112: 2735-2752.
7. Boutaud, O., J. Li, I. Zagol, E. A. Shipp, S. S. Davies, L. J. Roberts, 2nd, and J. A. Oates. 2003. Levuglandinyl adducts of proteins are formed via a prostaglandin $H_2$ synthase-dependent pathway after platelet activation. *J. Biol. Chem.* 278: 16926-16928.
8. Sugimori, H., F. Tomoda, T. Koike, H. Kinuno, H. Kurosaki, T. Masutani, and H. Inoue. 2012. Blood rheology and platelet function in untreated early-stage essential hypertensives complicated with metabolic syndrome. *Int J Hypertens* 2012: 109830.
9. Santilli, F., N. Vazzana, R. Liani, M. T. Guagnano, and G. Davi. 2012. Platelet activation in obesity and metabolic syndrome. *Obes Rev* 13: 27-42.
10. Smith, J. P., E. V. Haddad, M. B. Taylor, D. Oram, D. Blakemore, Q. Chen, O. Boutaud, and J. A. Oates. 2012. Suboptimal inhibition of platelet cyclooxygenase-1 by aspirin in metabolic syndrome. *Hypertension* 59: 719-725.
11. Koike, Y., A. Yoneyama, J. Shirai, T. Ishida, E. Shoda, K. Miyazaki, S. Sunaga, R. Horie, K. Aoki, K. Koike, I. Ogata, T. Tahara, T. Kato, K. Nakahara, T. Kariya, and M. Higashihara. 1998. Evaluation of thrombopoiesis in thrombocytopenic disorders by simultaneous measurement of reticulated platelets of whole blood and serum thrombopoietin concentrations. *Thromb. Haemost.* 79: 1106-1110.
12. Faull, R. J., X. Du, and M. H. Ginsberg. 1994. Receptors on platelets. Methods Enzymol. 245: 183-194.
13. 2005. Heart disease and stroke statistics. *Am Heart Assoc Update*. Dallas, Tex.
14. Serebruany, V. L., A. Malinin, S. Ong, and D. Atar. 2008. Patients with metabolic syndrome exhibit higher platelet activity than those with conventional risk factors for vascular disease. *J Thromb Thrombolysis* 25: 207-213.
15. Vaduganathan, M., C. L. Alviar, M. E. Arikan, A. Tellez, S. Guthikonda, T. DeLao, J. F. Granada, N. S. Kleiman, C. M. Ballantyne, and E. I. Lev. 2008. Platelet reactivity and response to aspirin in subjects with the metabolic syndrome. *Am Heart J* 156: 1002 e1001-1002 e1007.
16. Vaidya, D., L. R. Yanek, N. Faraday, T. F. Moy, L. C. Becker, and D. M. Becker. 2009. Native platelet aggregation and response to aspirin in persons with the metabolic syndrome and its components. *Metab Syndr Relat Disord* 7: 289-296.
17. Arteaga, R. B., J. A. Chirinos, A. O. Soriano, W. Jy, L. Horstman, J. J. Jimenez, A. Mendez, A. Ferreira, E. de Marchena, and Y. S. Ahn. 2006. Endothelial microparticles and platelet and leukocyte activation in patients with the metabolic syndrome. *Am. J. Cardiol.* 98: 70-74.
18. Gokulakrishnan, K., R. Deepa, V. Mohan, and M. D. Gross. 2006. Soluble P-selectin and CD40L levels in subjects with prediabetes, diabetes mellitus, and metabolic syndrome—the Chennai Urban Rural Epidemiology Study. *Metabolism* 55: 237-242.
19. Natal, C., P. Restituto, C. Inigo, I. Colina, J. Diez, and N. Varo. 2008. The proinflammatory mediator CD40 ligand is increased in the metabolic syndrome and modulated by adiponectin. *J Clin Endocrinol Metab* 93: 2319-2327.
20. Pignatelli, P., V. Sanguigni, L. Lenti, D. Ferro, A. Finocchi, P. Rossi, and F. Violi. 2004. gp91phox-dependent expression of platelet CD40 ligand. *Circulation* 110: 1326-1329.
21. Ford, E. S., A. H. Mokdad, W. H. Giles, and D. W. Brown. 2003. The metabolic syndrome and antioxidant concentrations: findings from the Third National Health and Nutrition Examination Survey. *Diabetes* 52: 2346-2352.
22. Palmieri, V. O., I. Grattagliano, P. Portincasa, and G. Palasciano. 2006. Systemic oxidative alterations are associated with visceral adiposity and liver steatosis in patients with metabolic syndrome. *J Nutr* 136: 3022-3026.
23. Roberts, L. J., 2nd, B. J. Sweetman, N. A. Payne, and J. A. Oates. 1977. Metabolism of thromboxane $B_2$ in man. Identification of the major urinary metabolite. *J. Biol. Chem.* 252: 7415-7417.
24. Catella, F., and G. A. FitzGerald. 1987. Paired analysis of urinary thromboxane $B_2$ metabolites in humans. *Thromb Res* 47: 647-656.
25. McAdam, B. F., D. Byrne, J. D. Morrow, and J. A. Oates. 2005. Contribution of cyclooxygenase-2 to elevated biosynthesis of thromboxane $A_2$ and prostacyclin in cigarette smokers. *Circulation* 112: 1024-1029.
26. Fitzgerald, D. J., L. Roy, F. Catella, and G. A. FitzGerald. 1986. Platelet activation in unstable coronary disease. *N. Engl. J. Med.* 315: 983-989.
27. Lellouche, F., M. Martinuzzo, P. Said, J. Maclouf, and L. O. Carreras. 1991. Imbalance of thromboxane/prostacyclin biosynthesis in patients with lupus anticoagulant. *Blood* 78: 2894-2899.
28. Martinuzzo, M. E., R. R. Forastiero, L. Kordich, and L. O. Carreras. 2001. Increased lipid peroxidation correlates with platelet activation but not with markers of endothelial cell and blood coagulation activation in patients with antiphospholipid antibodies. *Br J Haematol* 114: 845-851.

29. Blache, D., T. Gautier, U. J. Tietge, and L. Lagrost. 2012. Activated platelets contribute to oxidized low-density lipoproteins and dysfunctional high-density lipoproteins through a phospholipase $A_2$-dependent mechanism. *FASEB J* 26: 927-937.
30. Choi, J. W., J. H. Kim, S. C. Cho, M. K. Ha, K. Y. Song, H. D. Youn, and S. C. Park. 2011. Malondialdehyde inhibits an AMPK-mediated nuclear translocation and repression activity of ALDH2 in transcription. *Biochem Biophys Res Commun* 404: 400-406.
31. Besler, C., K. Heinrich, L. Rohrer, C. Doerries, M. Riwanto, D. M. Shih, A. Chroni, K. Yonekawa, S. Stein, N. Schaefer, M. Mueller, A. Akhmedov, G. Daniil, C. Manes, C. Templin, C. Wyss, W. Maier, F. C. Tanner, C. M. Matter, R. *Corti*, C. Furlong, A. J. Lusis, A. von Eckardstein, A. M. Fogelman, T. F. Luscher, and U. Landmesser. 2011. Mechanisms underlying adverse effects of HDL on eNOS-activating pathways in patients with coronary artery disease. *J. Clin. Invest.* 121: 2693-2708.

It will be understood that various details of the presently disclosed subject matter can be changed without departing from the scope of the subject matter disclosed herein. Furthermore, the foregoing description is for the purpose of illustration only, and not for the purpose of limitation.

We claim:

1. A composition for reducing or substantially preventing platelet activation in drawn blood, comprising:
    an irreversible inhibitor of COX-1;
    a compound for blocking activation of the purinergic receptors;
    a compound for blocking the thromboxane receptor;
    a compound for increasing intracellular cAMP concentration; and
    a compound that blocks potassium-dependent coagulation factors.

2. The composition of claim 1, further comprising at least one compound that is an aldehyde scavenger.

3. The composition of claim 1, comprising: EDTA, aspirin, apyrase, carbaprostacyclin, and SQ 29,548.

4. The composition of claim 2, wherein the aldehyde scavenger is at least one compound of the following formula:

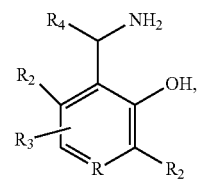

wherein:
    R is N or C;
    $R_2$ is independently H, substituted or unsubstituted alkyl;
    $R_3$ is H, halogen, alkoxy, hydroxyl, nitro;
    $R_4$ is H, substituted or unsubstituted alkyl, carboxyl; and
    pharmaceutically acceptable salts thereof.

5. The composition of claim 4, wherein the aldehyde scavenger is salicylamine.

6. A kit for reducing or substantially preventing platelet activation in drawn blood, comprising: a device for collecting blood, and the composition of claim 2.

7. The kit of claim 6, wherein the composition is contained within the device for collecting blood.

* * * * *